United States Patent [19]

Fontaine et al.

[11] Patent Number: 4,931,277

[45] Date of Patent: Jun. 5, 1990

[54] CAPSICUM AND POPULAS USEFUL FOR THE TREATMENT OF ALCOHOLIC TOXICOMANIA

[76] Inventors: Michel Fontaine, 82 rue Joseph Vallot, 74400 Chamonix, France; Marc Bonneau, 32 rue des Granges, 69005 Lyon, France

[21] Appl. No.: 149,227

[22] PCT Filed: May 12, 1987

[86] PCT No.: PCT/FR87/00155

§ 371 Date: Feb. 19, 1988

§ 102(e) Date: Feb. 19, 1988

[87] PCT Pub. No.: WO87/06834

PCT Pub. Date: Nov. 19, 1987

[30] Foreign Application Priority Data

May 12, 1986 [FR] France ................................. 86 0691

[51] Int. Cl.[5] ............................................. A61K 35/78
[52] U.S. Cl. .................................. 424/195.1; 514/811
[58] Field of Search ...................... 424/195.1; 514/811

[56] References Cited

U.S. PATENT DOCUMENTS

| | | | |
|---|---|---|---|
| 95,330 | 9/1869 | Drake | 424/195.1 X |
| 216,317 | 6/1879 | Du Rette | 424/195.1 |
| 257,029 | 4/1882 | Levings | 424/195.1 |
| 2,567,814 | 9/1951 | Jacobsen et al. | 514/476 |
| 4,368,206 | 1/1983 | Revici | 424/165 X |
| 4,565,689 | 1/1986 | Revici | 424/162 X |

OTHER PUBLICATIONS

Lust, *the Herb Book*, pp. 147–148, 311–313 (1974).

*Primary Examiner*—John W. Rollins
*Assistant Examiner*—Wendy Catchpole
*Attorney, Agent, or Firm*—Browdy & Neimark

[57] ABSTRACT

Medicaments for treatment of alcoholic toxicomania comprise at least one extract of vegetable origin, particularly those obtained by maceration, decoction and/or infusion in an aqueous alcoholic solvent of Capsicum peppers and/or bark or wood of Populus poplars. Preferably, the medicaments comprise mixtures containing 80% of extracts of *Capsicum pepper* and 20% of Populus extract formed by a mixture of small molecular weight molecules among which the predominant species exhibits a specific maximum absorption spectrum of 280 nm.

6 Claims, 3 Drawing Sheets

CAPSICUM AND POPULAS USEFUL FOR THE TREATMENT OF ALCOHOLIC TOXICOMANIA

FIELD OF THE INVENTION

This invention relates to new medicaments that can be used in human therapy as well as processes for obtaining them and their physicochemical and therapeutic characteristics.

These products are intended for the prevention and treatment of alcoholic toxicomania because of their pharmacological activities able to induce in most treated patients a loss of habit and even a disgust for alcoholic beverages.

BACKGROUND OF THE INVENTION

In our day alcoholism remains a medical and major social scourge. For example, in France in 1984, the annual average consumption of pure alcohol per inhabitant was 13.5 liters. Specialists estimate that for France the number of persons intoxicated by alcohol is five million, of whom two million are alcoholic and three million are excessive drinkers.

The medical, social and economic repercussions of alcoholic toxicomania was figured at an overall cost of about 75 billion francs for the French community for 1982: costs of sickness linked to alcoholism, work accidents, traffic accidents, premature deaths, loss of days of work, etc. . .

At present, actual alcoholic detoxication treatments used proceed from the use of the Antabuse effect of disulfiram and the use of the Dr. Champeau method (daily injection of 15% hypertonic solution of magnesium sulfate), both of which methods which aim at inducing an intolerance or a lack of habit for alcoholic beverages.

These treatments are difficult to use: there is risk of intoxication and secondary accidents due to disulfiram, restricting treatment for magnesium sulfate injections and risks of intolerance accidents. Despite these drawbacks, these treatments on an average make it possible to obtain about 50% good quality withdrawals in patients treated.

Besides their medical drawbacks, these antialcoholic treatments impose very heavy and very costly material, physical, psychological and institutional constraints on the community and public health economy. Further, they cause the alcoholic patient to be taken over totally: his detoxication rests on a principle of medical authority who tends to replace the patient's will and on a principle of sanctions linked to displeasures induced by ingestion of alcohol.

SUMMARY OF THE INVENTION

The inventors discovered that it was possible successfully to use, in antialcoholic cures, new medicaments consisting of extracts used either alone or in association and obtained from two vegetable species: the fruit of the pimento (Capsicum) and the wood and/or bark of the poplar (Populus).

The products according to the invention represent a notable advance relative to the preceding substances used in antialcoholic cures by the following characteristics:

They are products obtained by extraction and purification from vegetable substances. They are completely free of toxicity. Doses fifty times greater than therapeutic doses used in humans were administered to laboratory animals (mice, guinea pigs) without inducing notable toxic manifestations. Moreover, the vegetables from which these extracts are taken belong to the pharmacopeia and are known for their nontoxicity. On the other hand, their antialcoholic property is not known so far.

They are products that can be administered orally which do not require hospitalizing the patient. Further, these treatments can be used, without the patient's knowledge, by his family by adding the medicament to his usual drinks and foods. One daily dose is generally sufficient.

These treatments do not impose sudden alcoholic withdrawal; the patient to be detoxicated can have access to his usual alcoholic beverages whose consumption he gradually reduces as the therapeutic successes of the medicaments, which is the object of the invention, are felt.

These treatments give results qualitatively superior to those obtained by the present standard treatments cited above. The therapeutic successes marked by a good quality alcoholic withdrawal without relapse, can be figured at about 65 to 70% of cases treated.

Consequently, these treatments mark a notable advance both by the quality of their results and the low health cost which their use can bring about in comparison with existing treatments.

BRIEF DESCRIPTION OF THE DRAWINGS

The physicochemical characteristics of cayenne pepper and poplar extracts thus obtained will now be described with reference to the accompanying diagrammatic drawing, in which.

DETAILED DESCRIPTION OF THE INVENTION

Figure 1:
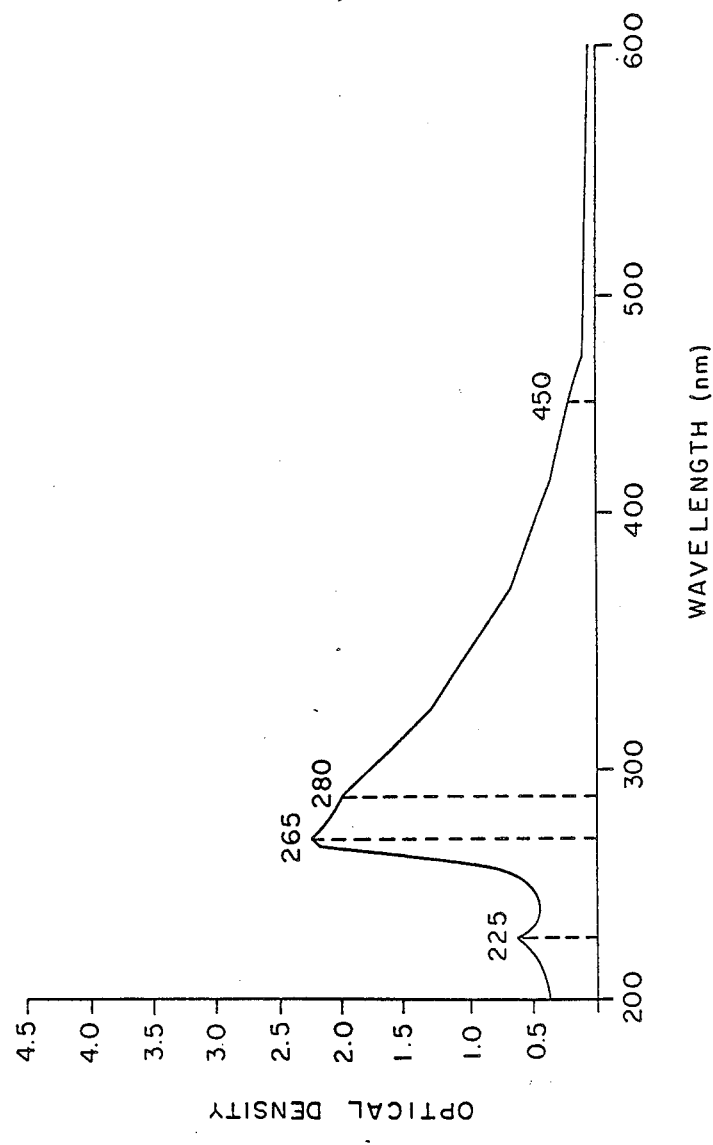
FIG. 1 represents the spectral analysis diagram of an extract of Capsicum annuum.

A process for preparing medicaments, object of the invention, consisting either of a simple extract or a mixture of vegetable extracts, will now be described in detail:

(a) PIMENTO (genus Capsicum—variety Capsicum annuum):

The first extract is obtained by maceration at ambient temperature, for ten days, of a volume of pulverulent grounds of the mature pimento fruit (genus Capsicum), in ten volumes of solvent consisting of a mixture of water-ethyl alcohol at 60° GL. The pulverulent grounds consist of particles exhibiting an average diameter on the order of 200 microns, and can also come from the leaves and stems of *Capsicum annuum*.

The ratio of pulverulent vegetable materials to extraction solvent can vary considerably, for example, up to one volume of Pimento grounds per twenty volumes of ethyl alcohol at 60°. The periods of maceration and alcoholic extraction can vary, while remaining effective, from several hours to several weeks.

The alcoholic extract of *Capsicum annuum* thus obtained is then clarified by centrifuging at 3000 g for 15 min at 4° C. The supernatant liquid is collected then filtered on sterilizing membranes and distributed in 10-ml stoppered bottles.

According to one of the variants of the process, the alcoholic extract of *Capsicum annuum* previously obtained can advantageously be fractionated by permeation chromatography, then purified and concentrated by ultrafiltration. The resulting concentrate can also be made pulverulent by freeze-drying, or desiccation under vacuum at low temperature.

The various parameters of the technical process described above are provided by way of example and are nonlimiting. Chemical solvents other than ethyl alcohol can also be used, such as acetic acid, for example. Also, the parameters relating to the physicochemical conditions of the extraction can vary: temperature, reaction time, concentration of reagents can be advantageously modified as a function of an extraction by maceration, of an extraction by decoction or an extraction by infusion.

The genus Capsicum, in all its wild or garden varieties, can be used.

(b) POPLAR (genus Populus—variety Populus Nigra):

The second extract, which is an object of the present invention, can be obtained according to a process of extraction and purification- concentration identical with that described above for *Capsicum annuum*.

The vegetable material used comes from grinding, into fine particles of 2 mm in diameter, bark, wood and leaves of Populus (preferably the variety *Populus nigra* or black poplar or Lombardy poplar). Extraction is obtained by maceration in ethyl alcohol at 60° for ten hours at ambient temperature.

The various extraction parameters provided by way of indication can vary and be differently associated in an advantageous way. For example, a simultaneous extraction by alcoholic maceration of the two vegetable grounds of pimento (genus Capsicum) and poplar (genus Populus) can also constitute a satisfactory variant of the preparation process, object of the invention.

(a) Extract of Pimento (genus Capsicum)

One millimeter of cayenne pepper extract, after evaporation of the alcoholic extraction phase, contains 13.9 mg of dry materials. Spectral analysis at different wavelengths (cf. FIG. 1) indicates that the pimento extract is characterized by the presence of different amounts of four different molecules whose respective characteristic absorption maxima are around 225 nm, 265 nm, 280 nm and 450 nm.

The quantitatively most abundant molecules in the extract are those characterized by respective maximum absorption spectra of 265 nm and 280 nm.

Analysis of the molecular weights of these molecules by permeation chromatography in phosphate buffer indicates that all these moleculas exhibit molecular respective weights equal to or less than 300 daltons.

(b) Extract of poplar (genus Populus)

Figure 2:
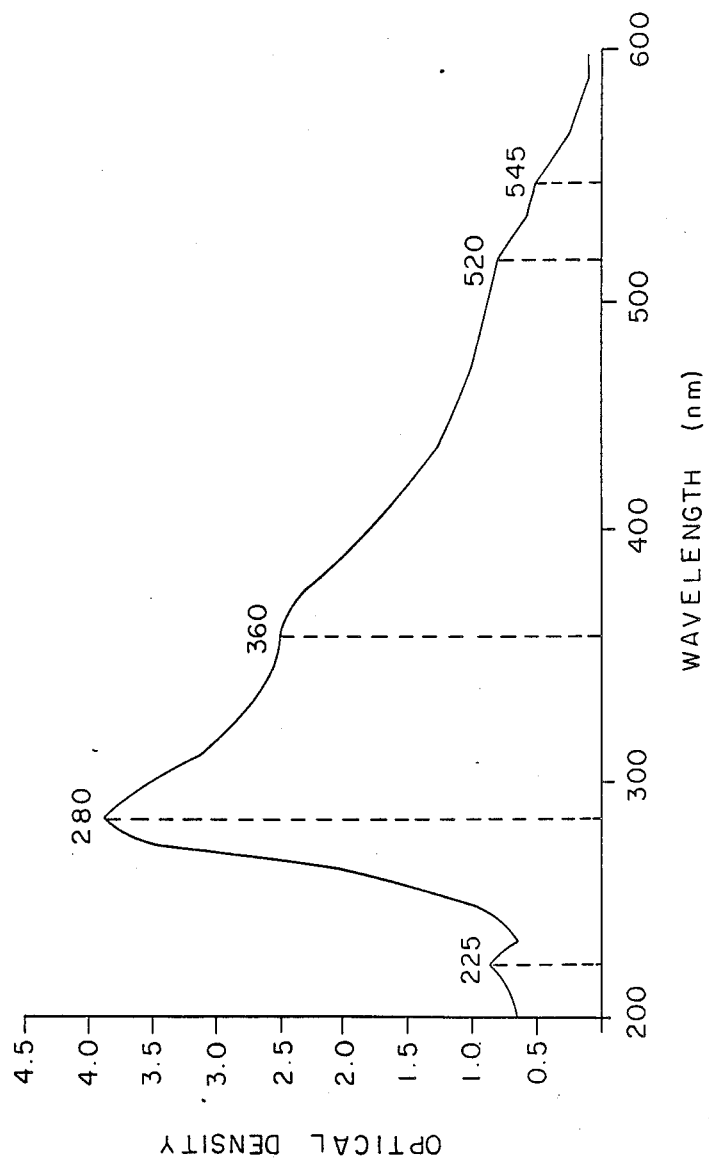
FIG. 2 is a view similar to FIG. 1 for the extract of Populus nigra.

One millimeter of extract of poplar, after evaporation of the extract alcoholic phase, contains 19.2 mg of dry materials. Spectral analysis at different wavelengths (cf. FIG. 2) indicates that the poplar extract is characterized by the presence of different amounts of five different molecules whose respective characteristic absorption maxima are around 225 nm, 280 nm, 360 nm, 520 nm and 545 nm.

The quantitatively most abundant molecules in the extract are those characterized by respective maximum absorption spectra of 280 nm and 360 nm.

The analysis of the molecular weights of these molecules by permeation chromatography in phosphate buffer indicates that all these molecules exhibit respective molecular weights equal to or less than 300 daltons.

Figure 3:
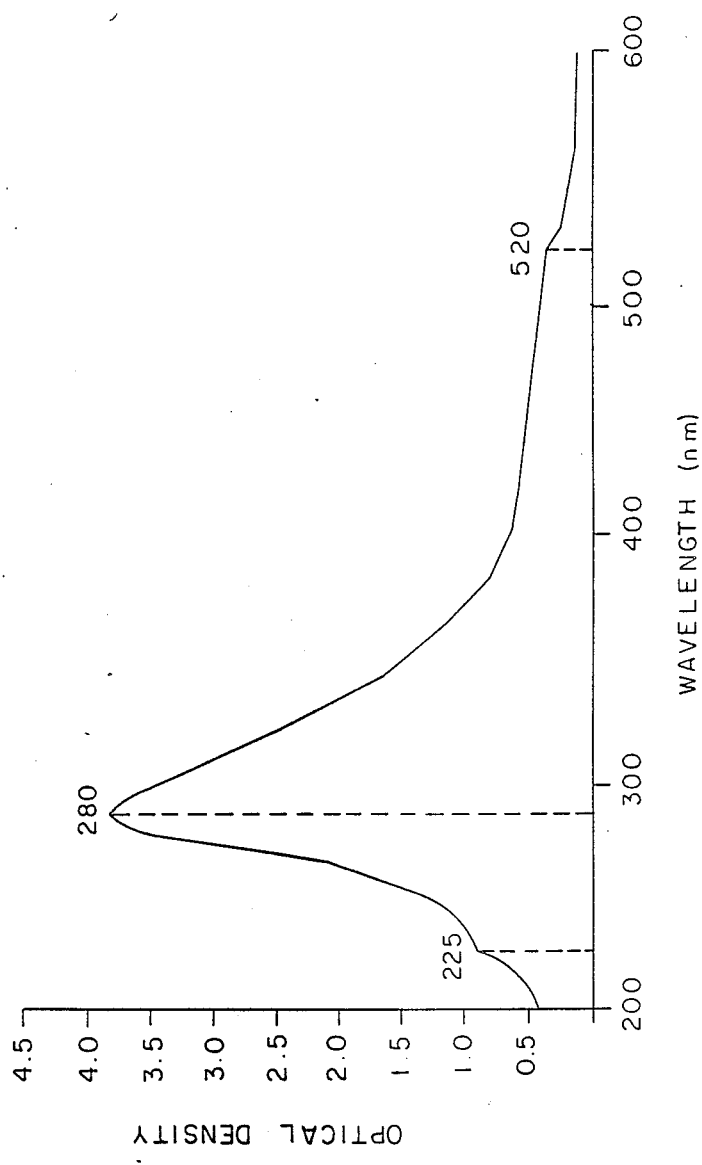
FIG. 3 is a view similar to FIGS. 1 and 2 for the mixture 4/5 Capsicum annuum, 1/5 Populus nigra.

| Sample number | nature of original plant | weight of 1 mm solution | dry weight of 1 ml of solution after evaporation |
|---|---|---|---|
| 1 | Pimento (*Capsicum annuum*) | 0.8085 g | 13.9 mg/ml |
| 2 | black poplar (*Populus nigra*) | 0.8540 g | 19.2 mg/ml |
| 3 (cf. FIG. 3) | 4/5 Capsicum annuum 1/5 Populus nigra | 0.8078 g | 14.5 mg/ml | the proportions of *Capsicum annuum* and *Populus nigra* are proportions by weight.

Galenic forms and dosages

One of the products according to the application will be presented by way of indication in two galenic forms coming from the above cited modes of preparation, either in the form of alcoholic solutions used separately or in association the alcoholic extracts of *Capsicum annuum* (fruit) and/or *Populus nigra* (bark and or wood), or in the form of dry extracts obtained by evaporation of the preceding solutions.

According to the modes of preparation used in this application the following dosages cited by way of indication correspond to the concentrations of the products obtained:

the alcoholic solutions of *Capsicum annuum*, of *Populus nigra* and of the mixture of *Capsicum annuum* (80% by volume) and *Populus nigra* (20% by volume) can be used, depending on the condition of the patient, in daily dosages going from 1 drop to 50 drops per days, with a therapeutic optimum around 5 drops per day.

The dry extract obtained by evaporation of the preceding alcoholic solutions are used in daily doses that can be spread out from 0.3 mg to 15 mg (50 drops of alcoholic solution correspond to 1 ml whose residual dry weight after evaporation is on the order of 13.9 mg to 19.2 mg in the examples cited above) distributed in the form of capsules or tablets or dragees.

Taking as the basic unit an average daily dosage of 5 drops of alcoholic solution, or 1.5 mg of dry residue, the capsules, tablets or dragees can be metered as units in this concentration cf extract. In this form, the dosage that can be used goes from one to ten capsules per day.

Pharmacological properties and therapeutic applications

Used in the above-cited daily doses, the separate or associated extracts of *Capsicum annuum* (fruit) and *Populus nigra* (bark and/or wood) either in liquid form or in the form of dry extract, when administered to chronic alcoholic patients, cause a progressive loss of habit in regard to alcoholic beverages. There either occurs a disgust for alcoholic beverages (10 to 20% of the positive cases) or a progressive loss of desire for these and loss of the pleasure and euphoria they procure (80 to 90% of positive cases). Then, in the case of positive result, there follows an abandonment of alcoholic beverages by the patients, which occurs in periods going from two to six weeks of treatment. If at the end of a month of actual treatment, no reduction of alcoholic beverages by the treated patient has started, the antialcoholic effect can no longer be hoped for from the treatment which then has failed.

Out of a first series of ten patients having received the medicaments according to the invention, there were obtained eight long-term withdrawals without relapse (backsliding between two and four years) and two failures. A second more recent series of fourteen patients treated according to the same methods confirmed the results previously obtained: twelve alcoholic withdrawals (backsliding between six and eighteen months) and two failures. In these two series, the therapeutic successes were objectivized by stopping of the dependence on alcoholic beverages, stopping of their consumption, disappearance of the clinical signs resulting from chronic alcoholism and by normalizing the biological parameters disturbed in chronic alcoholism, including gamma-glutamyl transpeptidase, and transaminases SGOT and SGPT (serum glutamate-oxacetate transaminase and serum glutimate-pyruvate transaminase).

By using the product in its optimal form which should correspond to a mixture associating 80% by volume of *Capsicum annuum* (fruit) extract and 20% by volume of *Populus nigra* (bark and/or wood) extract, it is possible to achieve 60 to 70% good quality alcoholic withdrawals in the patients treated.

The treatment should be continued for a minimal period of two months. It can be extended on request and repeated if necessary. In principle, it maintains its antialcoholic activity in case of relapse.

The treatment, undertaken with the help of the extracts, the object of the invention, does not cause any acute toxic effects nor undesirable secondary effects. However, considering that the medicaments, the object of the invention, contain Pimento, medical monitoring must be used in alcoholic patients who have shown or who show an ulcer type gastroduodenal pathology, to detect possible signs of intolerance which would lead to stopping the treatment.

This treatment can be administered to the patient, without his knowing it, by incorporation either in his food (after it has been cooked; heating above 60° C. destroys the product) or by mixing it in his beverages and particularly in his alcoholic beverages. The results of loss of habit appear approximately identical whether the patient know or does not know that this treatment is administered to him. A therapeutic effect of the placebo type therefore is ruled out.

Consequently, the patient can have access to alcoholic beverages during the treatment, which makes it possible to avoid authoritarian withdrawal measures (these measures minimize the beneficial effect giving value to stopping of the alcoholic toxicomania by substituting the patient's will with that of the medical team). In the most favorable cases, he comes to resume it himself, without alcohol, and without intervention of any outside authority replacing his free choice. This restores his confidence in himself, in his capacity of willing, of independence and success, which restores his value in his eyes and in the eyes of his associates. This point is very important considering the particular psychological profile of the alcoholic patient. It wipes out the derogatory view that the alcoholic has of himself in regard to his giving in to alcohol and his inability to face reality without the aid of this toxic; this view is one of the main factors responsible for the failure drive of the alcoholic which eventually causes him to fall back into his toxicomania and to fail in his social, professional and family life.

What is claimed is:

1. A method for treating alcoholic toxicomania comprising administering to a patient suffering from alcoholic toxicomania an effective amount of a composition containing an effective amount of an extract selected from extracts of the group consisting of the genus Capsicum, the genus Populus, and mixtures thereof.

2. The method according to claim 1 wherein the extract of genus Capsicum is obtained by a process selected from the group consisting of maceration, decoction, infusion, and combinations thereof, in an aqueous alcohol solution.

3. The method according to claim 2 wherein the composition contains 13.9 mg of dry active ingredient per ml of solvent, said dry material consisting of a mixture of molecules of molecular weight not greater than 300 D and which respectively exhibit a spectral absorption maximum at wavelengths of 225 nm, 265 nm, 280 nm, and 450 nm.

4. The method according to claim 1 wherein the extract of genus Populus is obtained by a process selected from the group consisting of maceration, decoction, infusion, and combinations thereof, in an aqueous alcohol solution.

5. The method according to claim 4 wherein the composition contains 19.2 mg of specific dry material per ml of solvent, said dry material consisting of a mixture of molecules of molecular weight not greater than 300 D and which respectively exhibit a spectral absorption maximum at wavelengths of 225 nm, 280 nm, 360 nm, 520 nm, and 545 nm.

6. The method according to claim 1 wherein the composition comprises 80% extract of cayenne pepper of the genus Capsicum and 20% of extract of Populus.

* * * * *